United States Patent [19]

Purcell

[11] Patent Number: 4,492,709
[45] Date of Patent: Jan. 8, 1985

[54] 2-[4(3)-AMINO-3(4)-HYDROXY-PHENYLIMINO]-IMIDAZOLINES, USEFUL IN THE TREATMENT OF GASTRIC HYPERSECRETION AND HYPERACIDITY

[75] Inventor: Thomas A. Purcell, Fontenay aux Roses, France

[73] Assignee: Synthelabo, Paris, France

[21] Appl. No.: 460,993

[22] Filed: Jan. 25, 1983

[30] Foreign Application Priority Data

Feb. 5, 1982 [FR] France .................. 82 01877

[51] Int. Cl.³ .................. A61K 31/415; C07D 231/06
[52] U.S. Cl. .................. 424/273 R; 548/315
[58] Field of Search .................. 548/315; 424/273 R

[56] References Cited

U.S. PATENT DOCUMENTS 3,818,094 6/1974 Stahle et al. .................. 424/273 R
4,262,005 4/1981 McCarthy et al. .................. 548/315
4,290,971 9/1981 Georgiev et al. .................. 548/315
4,414,223 11/1983 Copp et al. .................. 424/273 R Primary Examiner—Henry R. Jiles
Assistant Examiner—Kurt G. Briscoe
Attorney, Agent, or Firm—Wegner & Bretschneider

[57] ABSTRACT

Imidazolidine derivatives of the formula:

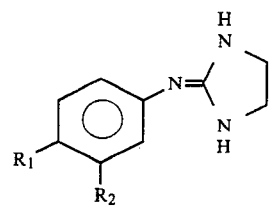

wherein $R_1$ represents the hydroxy radical and $R_2$ represents a grouping —$NHSO_2CH_3$, —NHCOR' or —NHCONR'R", R' and R" independently of one another representing a hydrogen atom or an alkyl radical having from 1 to 4 carbon atoms, or alternatively $R_2$ represents the hydroxy radical and $R_1$ represents a grouping —$NHSO_2CH_3$, —NHCOR' or ?NHCONR'R", R' and R" independently of one another representing a hydrogen atom or an alkyl radical having from 1 to 4 carbon atoms, and pharmacologically-acceptable acid addition salts thereof, are new therapeutically useful compounds. They are more particularly useful in the treatment of gastric hypersecretion or hyperacidity or glaucoma.

8 Claims, No Drawings

2-[4(3)-AMINO-3(4)-HYDROXYPHENYLIMINO]-IMIDAZOLINES, USEFUL IN THE TREATMENT OF GASTRIC HYPERSECRETION AND HYPERACIDITY

DESCRIPTION

This invention relates to new therapeutically useful imidazolidine derivatives, to processes for their preparation and to pharmaceutical compositions containing them.

The imidazolidine derivatives of the present invention are those compounds of the general formula:

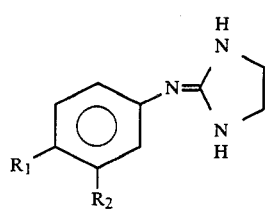

wherein $R_1$ represents the hydroxy radical and $R_2$ represents a grouping —NHSO$_2$CH$_3$, —NHCOR' or —NHCONR'R", R' and R" independently of one another representing a hydrogen atom or an alkyl radical having from 1 to 4 carbon atoms, or alternatively $R_2$ represents the hydroxy radical and $R_1$ represents a grouping —NHSO$_2$CH$_3$, —NHCOR' or —NHCONR'R", R' and R" independently of one another representing a hydrogen atom or an alkyl radical having from 1 to 4 carbon atoms, and their pharmacologically-acceptable acid addition salts.

The tautomeric forms of the compounds of general formula (I) are part of the present invention.

The preferred compounds are those wherein $R_1$ in general formula (I) represents the hydroxy radical, and more particularly those wherein $R_2$ represents the grouping —NHCHO, —NHSO$_2$CH$_3$ or —NHCONH$_2$, and pharmacologically-acceptable acid addition salts thereof. The most preferred compound of the present invention is 2-(3-formylamino-4-hydroxyphenylmino)-imidazolidine.

According to a feature of the present invention, those imidazolidine derivatives of general formula (I) wherein $R_1$ represents the hydroxy radical are prepared by the process illustrated in the following reaction scheme:

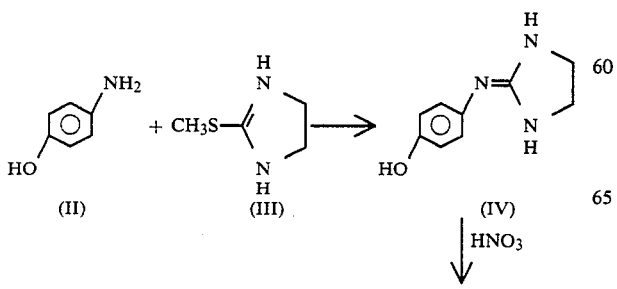

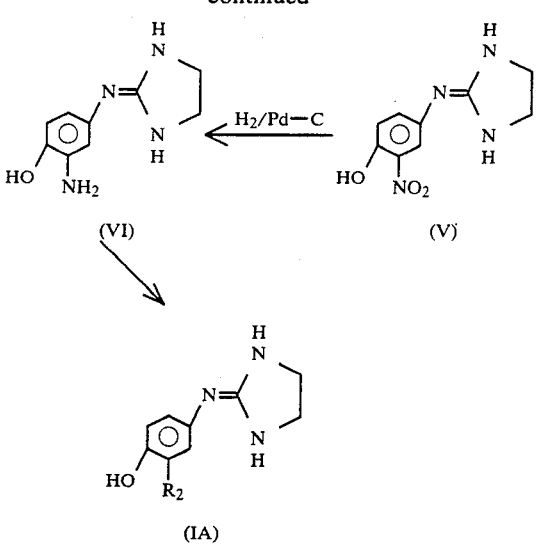

wherein $R_2$ is as hereinbefore defined when $R_1$ is the hydroxy radical.

According to the reaction scheme, p-hydroxyaniline is reacted with 2-methylthioimidazoline (optionally in the form of an acid addition salt such as the hydrochloride), for example in an organic solvent such as pyridine, to give 2-(4-hydroxyphenylimino)-imidazolidine, which is nitrated with nitric acid to give 2-(4-hydroxy-3-nitrophenylimino)-imidazolidine; this compound (formula V) is hydrogenated in the presence of a hydrogenation catalyst, such as palladium-on-charcoal, to give 2-(3-amino-4-hydroxyphenylimino)-imidazolidine, which is reacted with formic acid in the presence of acetic anhydride, or with methylsulphonyl chloride, or with a compound NaNCO or R'NCO (wherein R' represents an alkyl radical having from 1 to 4 carbon atoms) to obtain an imidazolidine derivative of general formula (IA).

According to a further feature of the present invention, those imidazolidine derivatives of general formula (I) wherein $R_2$ represents the hydroxy radical are prepared by the process illustrated in the following reaction scheme:

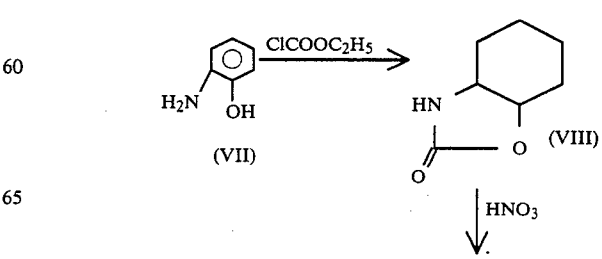

-continued

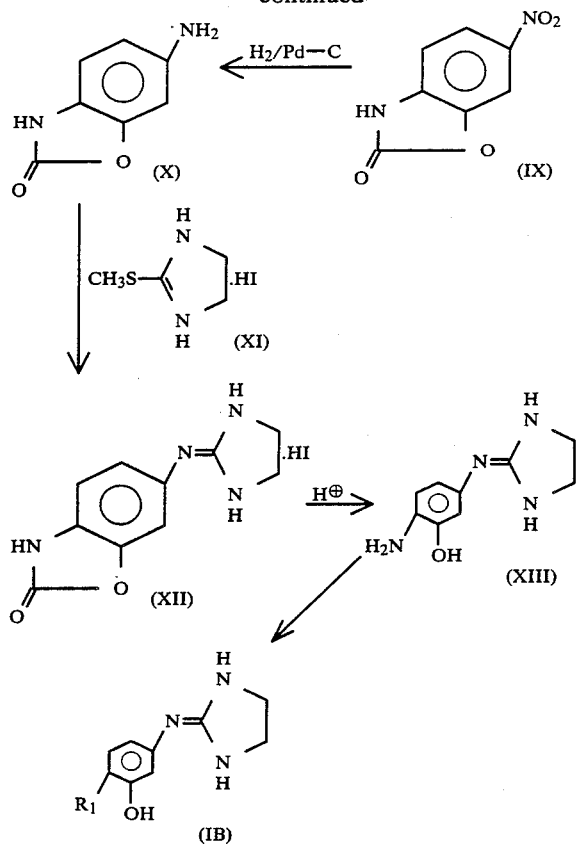

wherein R₁ is as hereinbefore defined when R₂ is the hydroxy radical.

According to the reaction scheme, o-aminophenol is reacted with ethyl chloroformate, the resulting 3H-benzoxazol-2-one obtained is nitrated with nitric acid, the nitro group of the resulting compound of formula (IX) is reduced with hydrogen in the presence of a hydrogenation catalyst, such as palladium-on-charcoal, the 6-amino-3H-benzoxazol-2-one thus obtained is reacted with 2-methylthioimidazoline, preferably in the form of an acid addition salt such as the hydroiodide, and the resulting compound of formula (XII) is acidified to give 2-(4-amino-3-hydroxyphenylimino)-imidazolidine, which is reacted with formic acid in the presence of acetic anhydride, or with methylsulphonyl chloride, or with a compound NaNCO or R'NCO (wherein R' represents an alkyl radical having from 1 to 4 carbon atoms) to obtain an imidazolidine derivative of general formula (IB).

Pharmacologically-acceptable acid addition salts of the imidazolidine derivative of general formula (I), e.g. methanesulphonates, mandelates, fumarates, maleates, malonates, citrates, hydrochlorides, hydrobromides and hydroiodides, may be obtained by methods known per se, for example by treatment of the imidazolidine base with the appropriate acid in a solvent medium, e.g. an alkanol or ether, or mixtures thereof.

By the term 'methods known per se' as used in this specification is meant methods heretofore used or described in the literature.

The following Examples illustrate the preparation of imidazolidine derivatives of general formula (I).

The analyses and the IR and NMR spectra confirm the structure of the compounds.

EXAMPLE 1

2-(3-Formylamino-4-hydroxyphenylimino)-imidazolidine and its hydrochloride (R₁=OH; R₂=—NHCHO)

1. 2-(4-Hydroxyphenylimino)-imidazolidine hydrochloride.

A mixture of 16.35 g (0.15 mol) of 4-hydroxyaniline and 38.4 g of 2-methylthioimidazoline hydrochloride in 150 cc of pyridine is heated at the reflux temperature for 2 hours. The thiol formed is trapped with KMnO₄ in dilute sulphuric acid. After standing overnight, the reaction mixture is poured into diethyl ether and washed with diethyl ether. The mixture is taken up in ethanol. Petroleum ether is added and the crystals formed are filtered off. 2-(4-Hydroxyphenylimino)-imidazolidine hydrochloride, melting at 220°-222° C., is obtained.

2. 2-(4-Hydroxy-3-nitrophenylimino)-imidazolidine hydrochloride.

13.25 g (0.0489 mol) of 2-(4-hydroxyphenylimino)-imidazolidine hydrochloride are introduced into 200 cc of acetic acid at ambient temperature, and 3.14 cc of nitric acid (specific gravity 1.42) are added. After 10 to 15 minutes the reaction mixture is poured into diethyl ether. After filtration and recrystallisation from ethanol, 2-(4-hydroxy-3-nitrophenylimino)-imidazolidine hydrochloride, melting at 231°-233° C., is obtained.

3. 2-(3-Amino-4-hydroxyphenylimino)-imidazolidine hydrochloride.

3.5 of 2-(4-hydroxy-3-nitrophenylimino)-imidazolidine hydrochloride are hydrogenated in a Parr apparatus, under a pressure of 50 psi, in 80 cc of dimethylformamide in the presence as catalyst of 10% palladium-on-charcoal.

After the catalyst has been removed, the reaction mixture is poured into diethyl ether and the supernatant is decanted. After the addition of ethanol and petroleum ether to the residue, the crystals formed are filtered off to give 2-(3-amino-4-hydroxyphenylimino)-imidazolidine hydrochloride melting at 217° C.

4. 2-(3-Formylamino-4-hydroxyphenylimino)-imidazolidine hydrochloride.

5 cc of formic acid and 0.4 cc of acetic anhydride are introduced into a round-bottomed flask and stirred for 15 minutes at 0° C. 914 mg (4 millimols) of 2-(3-aminio-4-hydroxyphenylimino)-imidazolidine hydrochloride are then added. The reaction mixture is stirred for 30 minutes and then poured into diethyl ether. The precipitate is filtered off and recrystallised from a mixture of ethanol/petroleum ether. The hydrochloride of 2-(3-formylamino-4-hydroxyphenylimino)-imidazolidine, melting at 226° C. (decomposition), is thus obtained.

EXAMPLE 2

2-(3-Aminocarbonylamino-4-hydroxyphenylimino)-imidazolidine and its hydrochloride (R₁=—OH; R₂=—NHCONH₂)

914 mg (4 millimols) of 2-(3-amino-4-hydroxyphenylimino)-imidazolidine hydrochloride (prepared as described in steps 1, 2 and 3 in Example 1) and 260 mg (4.32 millimols) of NaNCO are reacted together in a mixture of 6 cc of acetic acid and 4 cc of water. The reaction mixture is kept at 40° C. for 1 hour. It is then evaporated to dryness and the residue is taken up in water. The reaction mixture is chromatographed on an Amberlite IRC 50 column. After evaporation, the residue is taken up in ethanol, and a mixture of diethyl ether/hydrochloric acid is added. After recrystallisation from ethanol, 2-(3-aminocarbonylamino-4-hydroxyphenylimino)-imidazolidine hydrochloride, melting at 227° C. (decomposition), is obtained.

EXAMPLE 3

2-(4-Formylamino-3-hydroxyphenylimino)-imidazolidine and its hydrochloride ($R_1$=—NHCHO; $R_2$=—OH)

1. 3H-benzoxazol-2-one 38.4 cc (0.4 mol) of ethyl chloroformate are added, at a temperature between 0° and 10° C., to a solution of 38.4 g (0.35 mol) of o-aminophenol in 150 cc of pyridine. When the addition has ended, the reaction mixture is stirred for a further 2 hours and then poured into 1.5 liters of diethyl ether. The precipitate is filtered off. The ether in the filtrate is evaporated off on a rotary evaporator. The residue is heated to 180° C. in order to distill off the pyridine. After cooling, the residue is recrystallized from ethyl acetate. The melting point of the obtained compound is 136° C.

2. 6-Nitro-3H-benzoxazol-2-one 35 g (0.26 mol) of the compound obtained in step 1 are introduced into 300 cc of acetic acid, and 19 cc of nitric acid (specific gravity 1.42; 70% strength) are added at ambient temperature with stirring. The reaction mixture is heated gradually to 100° C. and kept at this temperature for 1 hour. It is then cooled to 20° C. and the solid is filtered off and washed with acetic acid and then with diethyl ether. The compound obtained melts at 243° C.

3. 6-Amino-3H-benzoxazol-2-one

A suspension of 10 g of the compound obtained in step 2 in 250 cc of ethanol, and 1 g of 10% palladium-on-charcoal, are introduced into a Parr apparatus under a hydrogen pressure of 30 psi. After filtering off the catalyst, the filtrate is evaporated to dryness on a rotary evaporator. The residue is washed with ethanol. This gives the amine, which is then used in the next step.

4. 6-(Imidazolidin-2-ylidene-amino)-3H-benzoxazol-2-one hydroiodide 13 g (86.7 millimols) of the compound obtained in step 3 and 22.2 g of 2-methylthio-2-imidazoline hydroiodide are heated to the reflux temperature in 100 cc of pyridine. The reflux is maintained until the evolution of methanethiol has ceased (about 2–3 hours). When the reaction has ended, the cooled mixture is poured into 1.5 liters of diethyl ether. The gummy residue is washed 3 times with 300 cc of diethyl ether and taken up in 100 cc of ethanol. The product is filtered off and recrystallised from methanol. Its melting point is 270°–272° C.

5. 2-(4-Amino-3-hydroxyphenylimino)-imidazolidine dihydrochloride.

1.2 g of the compound obtained in step 4 are dissolved in the minimum amount of water (120 cc) and the solution is treated with Amberlite resin (Cl$^-$) in chloroform. The aqueous phase is evaporated to dryness on a rotary evaporator. The residue is taken up in 50 cc of concentrated hydrochloric acid and the mixture is heated at the reflux temperature for about 32 hours. The reaction medium is then evaporated to dryness on a rotary evaporator and the residue is recrystallised from ethanol. The melting point of the obtained compound is 283° C.

6. 2-(4-Formylamino-3-hydroxyphenylimino)-imidazolidine hydrochloride.

2.2 g of the compound obtained in step 5 are dissolved in about 70 cc of water. The solution obtained is stirred with a solution of 50 cc of Amberlite L A 2 resin in 150 cc of toluene. The aqueous phase is decanted, washed with toluene and evaporated to dryness on a rotary evaporator. The residue is dried in vacuo over $P_2O_5$. This gives 2-(4-amino-3-hydroxyphenylimino)-imidazolidine monohydrochloride.

11 cc of formic acid are introduced into a 100 cc round-bottom flask and 0.875 cc of acetic anhydride is added at 0° C. The reaction mixture is stirred at 0° C. for 15 minutes and 2 g of the monohydrochloride obtained as described above are added all at once. The reaction mixture is then stirred at ambient temperature for 30 minutes and then poured into diethyl ether. The ether is removed and the residue is washed 3 times with diethyl ether. The residue is dissolved in ethanol, the solution treated with charcoal and crystallised from a mixture of ethanol/petroleum ether. The product is recrystallised from ethanol. Its melting point is 217° C. (decomposition).

The compounds of the invention which were prepared by way of examples are shown in the Table which follows.

TABLE

| Compound | $R_1$ | $R_2$ | Melting point (°C.) |
|---|---|---|---|
| 1 | —OH | —NHCHO | HCl - 226 (dec) |
| 2 | —OH | —NHSO$_2$CH$_3$ | HCl - 256 (dec) |
| 3 | —OH | —NHCONH$_2$ | HCl - 227 (dec) |
| 4 | —OH | —NHCONH—(CH$_2$)$_3$CH$_3$ | HCl - 193 |
| 5 | —NHCHO | —OH | HCl - 217 (dec) |
| 6 | —NHSO$_2$CH$_3$ | —OH | HCl - 230-231 |

The compounds of general formula (I) were studied pharmacologically, more particularly for their action on gastric secretion.

The acute toxicity of the compounds of the invention was determined by intraperitoneal administration to male mice of the CD strain; the toxicity is greater than 100 mg/kg animal body weight.

The effect on gastric activity was determined by the test carried out according to the modified version of Shay's technique (Gastroenterology 1945, 5, 43) described by Pascaud and Laubie (Arzneim. Forsch, 1971, 10, 1547).

Male CD rats weighing 200 to 250 g are deprived of solid food for 48 hours before the experiment and are divided up into randomised groups. The animals receive 4 ml of warm water physiological serum orally. They are then immediately anaesthetised with ether. After laparotomy, the gastric contents are evacuated via the duodenum by slightly compressing the stomach, and the pylorus is ligatured. Immediately afterwards, the compound to be studied, dissolved in physiological serum, is injected subcutaneously.

4 hours after ligature of the pylorus, the animals are sacrificed, the oesophagus is ligatured and the stomach is removed. The gastric contents are collected and centrifuged at 4000 G for 3 minutes. Any sample containing blood or a solid residue corresponding to a volume of more than 0.6 ml is discarded. The volume is measured and the acidity is evaluated using a solution of NaOH, the strength of which is such that 1 ml corresponds to 5 mg of HCl.

Two titrations are carried out:
1. up to the end point of dimethylaminoazobenzene (Topfer's reagent) at pH 3.5 (titration representing the "free" acidity).
2. up to the end point of phenolphthalein at pH 8.5 (titration representing the "total" acidity).

The results are expressed in $\mu$ equivalents/4 hours/100 g.

The compounds of the invention reduce the volume and the gastric acidity. At a dose of 0.1 mg/kg animal body weight the reduction ranges from 45 to 60%.

Furthermore, the compounds of the invention can be active in therapeutic applications in which stimulation of the α-adrenergic receptors is required; for example, the following applications can be envisaged:

vasoconstriction at the local level, in particular nasal decongestion, orthostatic hypotension of genetic or medicinal origin, glaucoma, gastric hypersecretion.

The invention consequently includes all types of pharmaceutical compositions containing, as active ingredient, an imidazolidine derivative of general formula (I), or a pharmacologically acceptable acid addition salt thereof, in association with any excipient suitable for oral or parenteral administration.

The compounds of general formula (I) can be presented in the form of tablets, coated tablets, gelatin capsules, ordinary capsules, solutions and suspensions to be taken orally, injectable solutions, and so on.

The daily dosage can range from 0.1 to 10 mg of active compound.

I claim:
1. An imidazolidine compound of the formula:

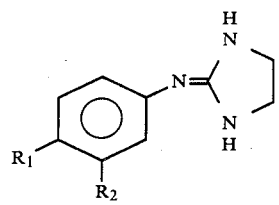

wherein $R_1$ represents the hydroxy radical and $R_2$ represents a grouping, —NHCOR' or —NHCONR'R", R' and R" independently of one another representing a hydrogen atom or an alkyl radical of 1 through 4 carbon atoms, or alternatively $R_2$ represents the hydroxy radical and $R_1$ represents a grouping —NHCOR' or —NHCONR'R", R' and R" independently of one another representing a hydrogen atom or an alkyl radical of 1 through 4 carbon atoms, and pharmacologically-acceptable acid additions salts thereof.

2. An imidazolidine compound according to claim 1 wherein $R_1$ represents the hydroxy radical and $R_2$ represents a grouping, —NHCOR' or —NHCONR'R", R' and R" independently of one another representing a hydrogen atom or an alkyl radical of 1 through 4 carbon atoms, and pharmacologically-acceptable acid addition salts thereof.

3. An imidazolidine compound according to claim 1 wherein $R_1$ represents the hydroxy radical and $R_2$ represents the grouping —NHCHO, or —NHCONH$_2$, and pharmacologically-acceptable acid addition salts thereof.

4. An imidazolidine compound according to claim 1 which is 2-(3-formylamino-4-hydroxyphenylimino)-imidazolidine, and pharmacologically-acceptable acid addition salts thereof.

5. An imidazolidine compound according to claim 1 which is 2-(3-aminocarbonylamino-4-hydroxyphenylimino)-imidazolidine, and pharmacologically-acceptable acid addition salts thereof.

6. An imidazolidine compound according to claim 1 which is 2-(4-formylamino-3-hydroxyphenylimino)-imidazolidine, and pharmacologically-acceptable acid addition salts thereof.

7. A composition for treating gastric hypersecretion or hyperacidity, which comprises an effective gastric hypersecretion or hyperacidity reducing amount of an imidazolidine compound of claim 1, or a pharmacologically-acceptable acid addition salt thereof, in association with a carrier.

8. A method for the treatment of a patient suffering from gastric hypersecretion or hyperacidity, which comprises administering to the patient a hypersecretion or hyperacidity reducing amount of an imidazolidine compound of claim 1, or a pharmacologically-acceptable acid addition salt thereof.

* * * * *